United States Patent
Alary et al.

(10) Patent No.: US 11,717,448 B2
(45) Date of Patent: Aug. 8, 2023

(54) MULTI-FUNCTIONAL PERSONALIZED PATCH WITH THERAPEUTIC PROPERTIES

(71) Applicant: Johnson & Johnson Consumer Inc., Skillman, NJ (US)

(72) Inventors: Marc Alary, Skillman, NJ (US); Jan-Joo Liu, Skillman, NJ (US); Bharat Patel, Skillman, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 873 days.

(21) Appl. No.: 16/625,155

(22) PCT Filed: Jun. 27, 2018

(86) PCT No.: PCT/IB2018/054771
§ 371 (c)(1),
(2) Date: Dec. 20, 2019

(87) PCT Pub. No.: WO2019/003152
PCT Pub. Date: Jan. 3, 2019

(65) Prior Publication Data
US 2021/0059860 A1    Mar. 4, 2021

Related U.S. Application Data

(60) Provisional application No. 62/525,425, filed on Jun. 27, 2017.

(51) Int. Cl.
*A61M 35/00* (2006.01)
*A61F 13/00* (2006.01)
(Continued)

(52) U.S. Cl.
CPC .. *A61F 13/00063* (2013.01); *A61F 13/00059* (2013.01); *A61F 13/0289* (2013.01);
(Continued)

(58) Field of Classification Search
CPC .......... A61F 13/00059; A61F 13/00063; A61F 13/0289; A61F 2013/00378;
(Continued)

(56) References Cited

U.S. PATENT DOCUMENTS 5,368,553 A    11/1994 Newman
5,382,433 A    1/1995 Pahlick et al.
(Continued)

FOREIGN PATENT DOCUMENTS

WO    WO 1991/007277 A    5/1991
WO    WO 2016/179610 A    11/2016

OTHER PUBLICATIONS

International search report dated Oct. 25, 2018, for international application PCT/IB2018/054771.
(Continued)

*Primary Examiner* — Camtu T Nguyen

(57) ABSTRACT

Carefully coordinated patches having camouflaging and/or benefit properties can be formed for application to a desired region of human skin. The patches include a flexible film having a first, adhesive, outwardly facing major surface and a second outwardly facing surface which is textured to correspond to skin covered by the patch during use; wherein the flexible film further comprises at least one pigmented region and at least one region adapted to modify one or more optical properties selected from the group consisting of light transmission, light reflection, and light absorption. Methods of custom use of such patches may include 3D printing processes.

4 Claims, 2 Drawing Sheets

(51) Int. Cl.
*A61F 13/02* (2006.01)
*A61K 9/70* (2006.01)
*A61K 45/06* (2006.01)

(52) U.S. Cl.
CPC ............ *A61K 9/7038* (2013.01); *A61K 45/06* (2013.01); *A61F 2013/00378* (2013.01); *A61F 2013/00846* (2013.01); *A61M 35/00* (2013.01)

(58) Field of Classification Search
CPC ........ A61F 2013/00846; A61K 9/7038; A61K 45/06; A61M 35/00
See application file for complete search history.

(56) References Cited

U.S. PATENT DOCUMENTS

| | | |
|---|---|---|
| 6,117,435 A | 9/2000 | Painter et al. |
| 6,394,613 B1 | 5/2002 | Hatakeyama et al. |
| 7,517,571 B2 | 4/2009 | Funke et al. |
| 2005/0255300 A1 | 11/2005 | Funke et al. |
| 2007/0010776 A1 | 1/2007 | Price et al. |
| 2007/0020323 A1 | 1/2007 | Horstmann |
| 2012/0029405 A1 | 2/2012 | Cataldi et al. |
| 2015/0157509 A1 | 6/2015 | Atkinson et al. |
| 2015/0190332 A1 | 7/2015 | Howell et al. |
| 2016/0377768 A1 | 12/2016 | Wilson et al. |

OTHER PUBLICATIONS

Yu et al., "An elastic second skin", *Nature Materials* (2016) 15:911-918.

MULTI-FUNCTIONAL PERSONALIZED PATCH WITH THERAPEUTIC PROPERTIES

CROSS-REFERENCE TO RELATED APPLICATIONS

This application is the national phase filing under 35 USC 371 of international application PCT/IB2018/054771 filed on Jun. 27, 2018, which claims the benefit of U.S. provisional application 62/525,425 filed on Jun. 27, 2017.

FIELD OF THE INVENTION

The present invention relates to a camouflage make-up patch for application to an individual's skin for hiding or concealing undesired skin characteristics. Specifically, the present invention is an adhesive patch for application to an individual's skin that mimics the appearance of the underlying skin and a method of using such a patch.

BACKGROUND OF THE INVENTION

Camouflage make-up is the art of covering up imperfections in the skin such as acne scars, and skin discolorations such as white patches on the skin, dermatitis that reddens the skin, and surgery scars. It's also called medical make-up, corrective camouflage make-up or camouflage make-up. It often comes in the form of creams and/or powders to conceal color or contour irregularities or abnormalities of the face or body.

Recently, there have been reported patches which cover the imperfections in a single layer, such as temporary tattoos, or pads, where the top surface of the pad is coated with a color matching pigment.

These methods, however, do not duplicate the natural skin color and optical properties of the skin and do not treat the unwanted skin condition.

There is a need for types of camouflage make-up that provide superior skin camouflage capabilities for unwanted skin conditions, providing excellent skin color matching and matching to the optical properties of a consumer's natural skin while delivering formulations and/or actives to treat the unwanted skin condition.

SUMMARY OF THE INVENTION

Surprisingly, we have found that carefully coordinated patches having camouflaging and/or benefit properties can be formed for application to a desired region of human skin. In one embodiment, the patch includes a flexible film having a first, adhesive, outwardly facing major surface and a second outwardly facing surface which is textured to correspond to skin covered by the patch during use; wherein the flexible film further comprises at least one pigmented region and at least one region adapted to modify one or more optical properties selected from the group consisting of light transmission, light reflection, and light absorption.

In another embodiment, the patch includes a first, adhesive, outwardly facing major surface; a second outwardly facing surface which is textured to correspond to skin covered by the patch during use; at least one pigmented layer; and at least one layer adapted to modify one or more optical properties selected from the group consisting of light transmission, light reflection, and light absorption.

In a further embodiment, the patch includes a flexible film having a first, outwardly facing adhesive layer, a second, outwardly facing major surface, opposite the first outwardly facing adhesive layer, which is textured to correspond to skin covered by the patch during use; wherein the flexible film further comprises, disposed between the first, outwardly facing adhesive layer and the second, outwardly facing major surface, at least one pigmented layer and at least one layer adapted to modify one or more optical properties selected from the group consisting of light transmission, light reflection, and light absorption.

In a fourth embodiment, the patch includes a plurality of layers, a first outer layer having an adhesive a first outer surface, second outer surface, first layer associated with adhesive layer; second outer layer having associated therewith at least one layer forming the textured surface, and at least one intermediate layer disposed between the first, adhesive layer and the second outer surface, the at least one intermediate layer having at least one pigmented region or layer and at least one region or layer adapted to modify one or more optical properties selected from the group consisting of light transmission, light reflection, and light absorption.

A fifth embodiment of the invention relates to a method of camouflaging a blemish in a desired region of human skin. The method includes the steps of: (a) providing image data relating to the desired region of human skin to a computer, wherein the computer converts the image data to geometric data representing a geometric model of the desired region of human skin; (b) using the geometric data to control a 3D printer to print successive layers of flexible materials to form a patch for application to the desired region of human skin comprising a flexible film having a first, adhesive, outwardly facing major surface and a second outwardly facing surface which is textured to correspond to skin covered by the patch during use; wherein the flexible film further comprises at least one pigmented region and at least one region adapted to modify one or more optical properties selected from the group consisting of light transmission, light reflection, and light absorption; and (c) applying the patch to the desired region of human skin.

DETAILED DESCRIPTION OF THE INVENTION

The present invention relates to a camouflage make-up patch to provide superior skin camouflage capabilities for unwanted skin conditions such as: pimples, scars, eczema and psoriasis. The following description is presented to enable one of ordinary skill in the art to make and use the invention. Various modifications to the embodiments and the generic principles and features described herein will be readily apparent to those skilled in the art. Thus, the present invention is not intended to be limited to the embodiments shown, but is to be accorded the widest scope consistent with the features described herein.

As used herein the specification and the claims, the term "topical" and variants thereof mean of or applied to an isolated part of the body. This includes, without limitation skin, mucosa, and enamel.

As used herein, "benefit agent" means an ingredient or material that provides a benefit, e.g., improves, relieves, reduces, or treats symptoms or conditions of the skin, ether cosmetic or therapeutic.

The method for treating common consumer skin flaws described herein uses a personalized camouflage patch which provides excellent skin color matching and maintains the optical properties of a consumer's natural skin. In some embodiments, it may also deliver formulations and/or actives to treat the unwanted skin condition. The patch has a multi-layer construction manufactured that provides optimal skin color, transparency, texture and opaque qualities to perfectly match a consumer's natural skin. The multi-layer construction provides a skin texture layer that matches the consumer's skin color, multiple light absorptive and reflective layers to mimic natural skin optical properties and one or more layers for formulation and active delivery to treat the skin and serves as the adhesive layer to hold the patch in place.

Figure 1:
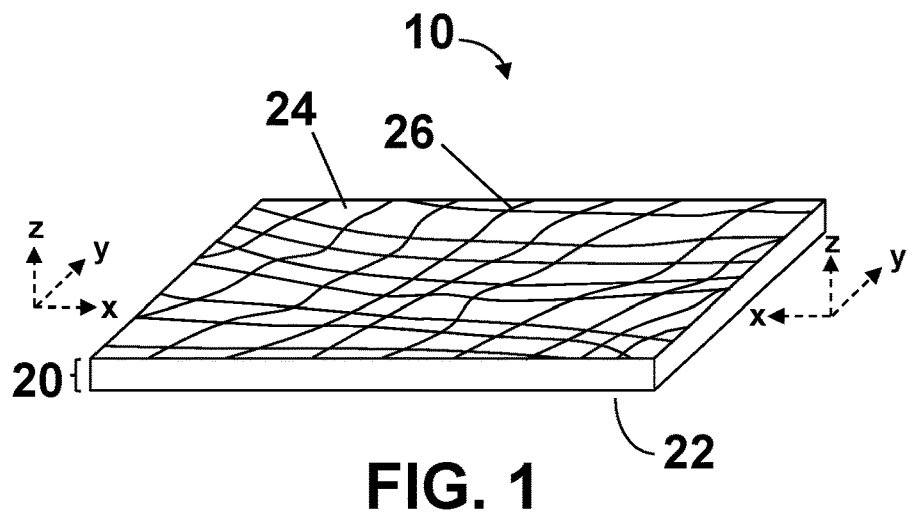
FIG. 1 is a perspective view of a first embodiment of a camouflage make-up patch of the present invention.
Figure 2:
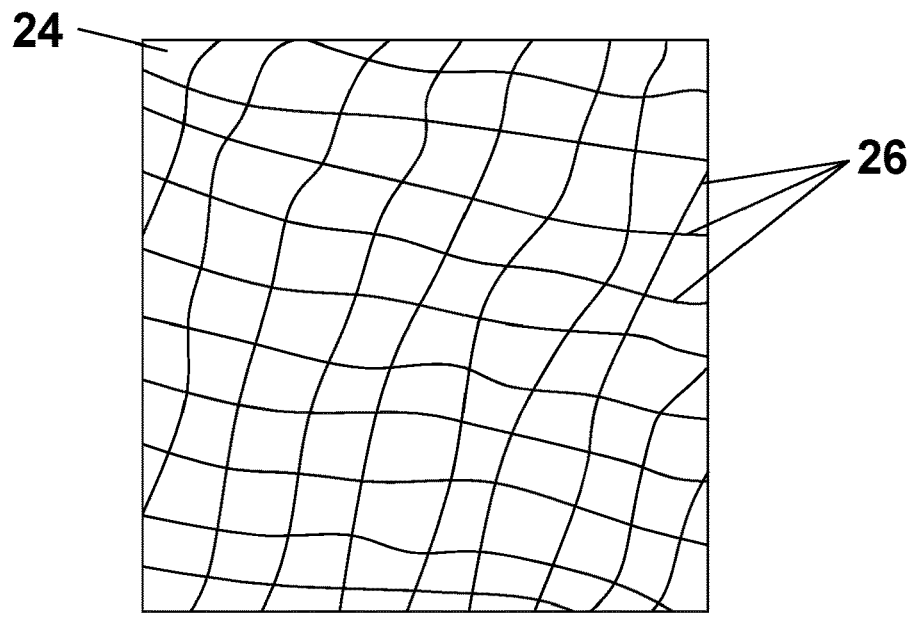
FIG. 2 is a top view of the camouflage make-up patch embodiment of FIG. 1.
Figure 3:
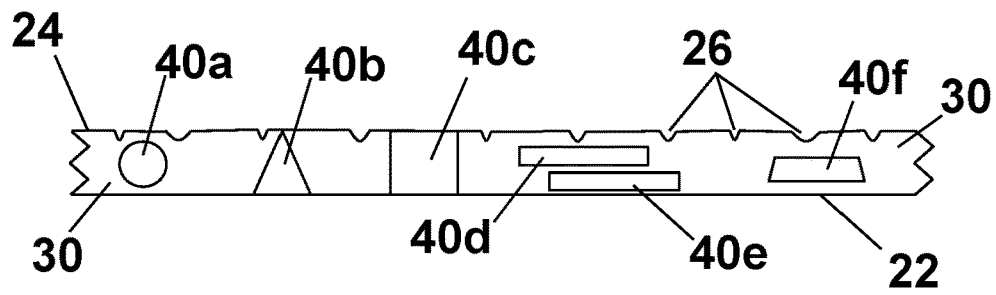
FIG. 3 is a cross-sectional view of the camouflage make-up patch embodiment of FIG. 1 in the x-z plane.

FIGS. 1 to 3 show a first embodiment of a camouflage make-up patch 10 of the present invention. FIG. 1 is a perspective view of patch 10, including a flexible film 20 having a first outwardly facing major surface 22, and a second outwardly facing major surface 24. First outwardly facing major surface 22 is adhesive to the skin of the user. Second outwardly facing major surface 24 has surface texture elements 26 to substantially correspond to the concealed skin. The thickness of patch 10 is between about 0.01 mm and about 1 mm.

FIG. 2 is a top view of camouflage make-up patch 10. The figure shows surface texture elements 26 on second outwardly facing major surface 24. FIG. 3 is a cross-sectional view of camouflage make-up patch 10 in the x-z plane. The figure shows flexible film 20 having a pigmented region 30, as well as regions containing optical modifying materials, which are termed optical modifying regions 40.

First outwardly facing major surface 22 is adhesive to the skin of the user. As used herein, "adhesive" means a material or substance that causes something to adhere, as in this case, to the skin of the user. In some embodiments, outwardly facing major surface 22 comprises a pressure sensitive adhesive layer.

FIGS. 1 to 3 show second outwardly facing major surface 24 with surface texture elements 26. As used herein, "texture" means the surface quality of major surface 24 are measure by the roughness or smoothness of the surface. In this embodiment, surface texture elements 26 on major surface 24 are shown as continuous lines of indentation on surface 24. It is to be understood that surface texture elements 26 may also include, but are not limited to, discontinuous indentation lines, indentation regions, as well as continuous or discontinuous surface bulge lines, surface bulge regions, and surfaces with both indentations and bulges.

Flexible film 20 has a pigmented region 30. Pigmented region 30 contains pigments for matching the color of the user's skin in the region of patch 10 application. Pigmented region 30 is formed by mixing colorants into a matrix of a relatively neutral or colorless material. Details regarding colorants and matrix materials will be discussed henceforth.

Also, flexible film 20 has optical modifying regions 40. The materials in these regions may modify one or more of the following optical properties: light transmission, light reflection, and light absorption. FIG. 3 shows optical modifying regions 40 having a number of cross-sectional geometries. These include oval (40a), triangular (40b), square (40c), rectangular (40d and 40e), and trapezoidal (40f). In some embodiments, optical modifying regions, such as regions 40b and 40c, span from first outwardly facing major surface 22 to second outwardly facing major surface 24. In some embodiments, optical modifying regions, such as regions 40d and 40e, span are stacked between first outwardly facing major surface 22 and second outwardly facing major surface 24.

Optical modifying regions 40 are formed by mixing optical modifiers into a matrix of a relatively neutral or colorless material. Details regarding optical modifiers and matrix materials will be discussed henceforth.

Pigmented region 30 is shown in FIG. 3 as continuous, with regions 40 being discrete. In some embodiments, pigmented region 30 may be discrete, with regions 40 being continuous. In other embodiments, flexible film 20 may have both continuous and discrete pigmented region 30, as well as continuous and discrete optical modifying regions 40.

In use, flexible film 20 comprising patch 10 is arranged and configured to cover a skin blemish. Here, the pigmented region 30 and at least one optical modifying region 40 (region adapted to modify one or more optical properties) are arranged and configured to correspond to unblemished skin.

Figure 4:
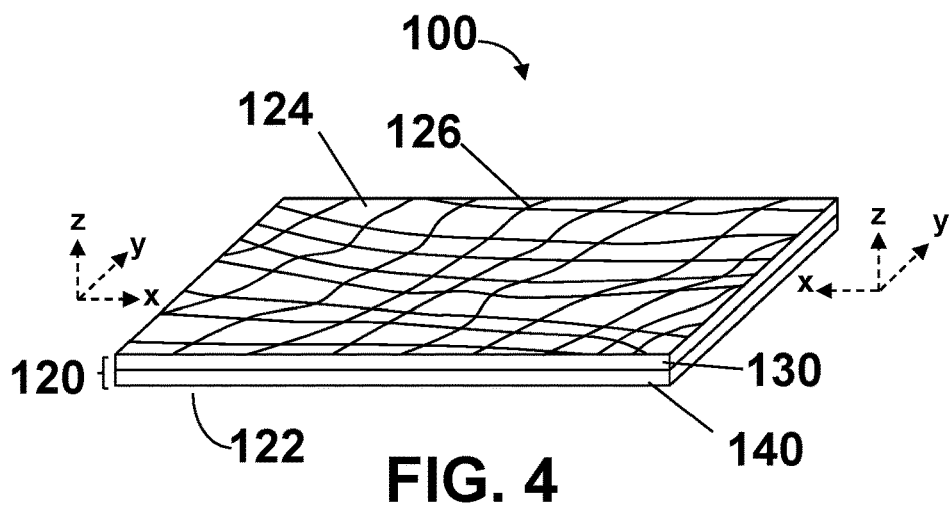
FIG. 4 is a perspective view of a second embodiment of a camouflage make-up patch of the present invention.
Figure 5:
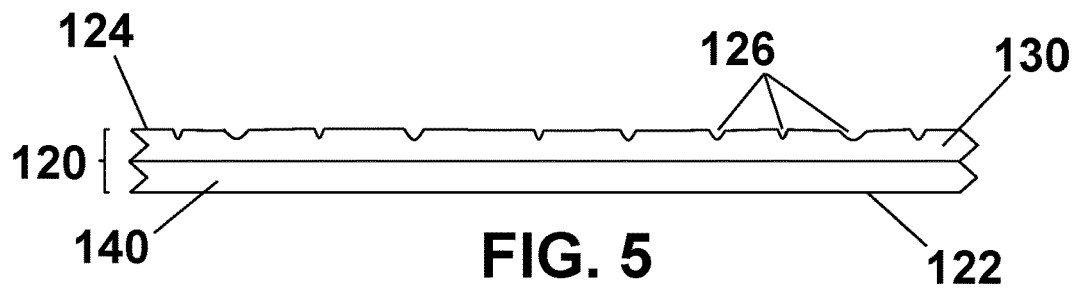
FIG. 5 is a cross-sectional view of the camouflage make-up patch embodiment of FIG. 4 in the x-z plane.

FIGS. 4 and 5 show a second embodiment of a camouflage make-up patch 100 of the present invention. FIG. 4 is a perspective view of patch 100, while FIG. 5 is a cross-sectional view of camouflage make-up patch 100 in the x-z plane. The figures show patch 100 having a flexible film 120 having a first outwardly facing major surface 122, and a second outwardly facing major surface 124. First outwardly facing major surface 122 is adhesive to the skin of the user. In some embodiments, outwardly facing major surface 122 comprises a pressure sensitive adhesive layer. Second outwardly facing major surface 124 has surface texture elements 126 to substantially correspond to the concealed skin. The figures also show flexible film 120 having a pigmented layer 130, as well as a layer containing optical modifying materials, which is termed optical modifying layer 140.

Second outwardly facing major surface 124 has surface texture elements 126, shown as continuous lines of indentation on surface 124.

Flexible film 120 has pigmented layer 130 containing pigments for matching the color of the user's skin in the region of patch 100, and optical modifying layer 140. The materials in layer 140 may modify one or more of the following optical properties: light transmission, light reflection, and light absorption.

FIGS. 4 and 5 show and embodiment of camouflage make-up patch 100 with a single pigmented layer 130 as well as a single optical modifying layer 140. In other embodiments, patch 100 may have multiple pigmented 130 and/or optical modifying 140 layers. The figures also show that in the present embodiment, pigmented layer 130 is adjacent to second outwardly facing major surface 124, while optical modifying layer 140 is adjacent to first outwardly facing major surface 122. In other embodiments, patch 100 may have pigmented layer 130 adjacent to first outwardly facing major surface 122, while optical modifying layer 140 is adjacent to second outwardly facing major surface 124. In still other embodiments, where there are multiple pigmented 130 and/or optical modifying 140 layers, there may be pigmented layers 130, or optical modifying 140 layers, adjacent to both first outwardly facing major surface 122 or second outwardly facing major surface 124.

In some embodiments, pigmented layer 130 is continuously pigmented, while in other embodiments, pigmented layer 130 has discrete pigmented regions separated by non-pigmented regions. In still other embodiments, pigmented layer 130 has at least one first pigmented region and at least one second pigmented region, wherein the first and second pigmented regions are differently pigmented.

In use, flexible film 120 comprising patch 100 is arranged and configured to cover a skin blemish. Here, the pigmented layer 130 and at least one optical modifying layer 140 (region adapted to modify one or more optical properties) are arranged and configured to correspond to unblemished skin.

Figure 6:
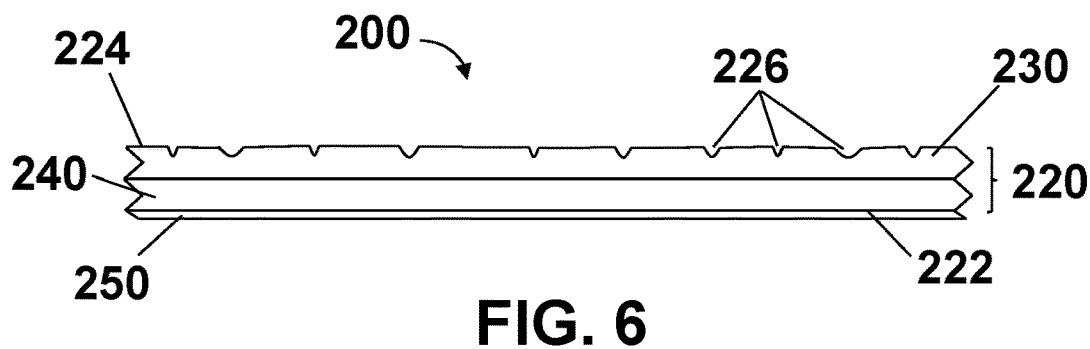
FIG. 6 is a cross-sectional view of a third embodiment of a camouflage make-up patch of the present invention in the x-z plane.

FIG. 6 is a cross-sectional view of a third embodiment of a camouflage make-up patch 200 of the present invention in the x-z plane. The figure shows patch 200 having a flexible film 220 having a first outwardly facing major surface 222, and a second outwardly facing major surface 224. First outwardly facing major surface 222 has an adhesive layer 250 so as to be adhesive to the skin of the user. Adhesive layer 250 may be a continuous layer of adhesive, or may have discrete regions of adhesive. In some embodiments, adhesive layer 250 may be a pressure sensitive adhesive. Second outwardly facing major surface 224 has surface texture elements 226 to substantially correspond to the concealed skin. The figure also shows flexible film 220 having a pigmented layer 230, as well as a layer containing optical modifying materials, which is termed optical modifying layer 240.

The surface texture elements 226 on second outwardly facing major surface 224 are shown as continuous lines of indentation on surface 224, but as discussed previously, they may be discontinuous indentation lines, indentation regions, as well as continuous or discontinuous surface bulge lines, surface bulge regions, and surfaces with both indentations and bulges.

Flexible film 220 has pigmented layer 230 containing pigments for matching the color of the user's skin in the region of camouflage make-up patch 200, and optical modifying layer 240. The materials in layer 240 may modify one or more of the following properties: light transmission, light reflection, and light absorption.

Also as discussed earlier, third embodiment of camouflage make-up patch 200 has a single pigmented layer 230 as well as a single optical modifying layer 240. In other embodiments, patch 200 may have multiple pigmented 230 and/or optical modifying 240 layers. Also, pigmented layer 230 is shown adjacent to second outwardly facing major surface 224, and optical modifying layer 240 is adjacent to first outwardly facing major surface 222. In other embodiments, the pigmented layer 230 may be adjacent to first outwardly facing major surface 222, while optical modifying layer 240 may be adjacent to second outwardly facing major surface 224. In other embodiments with multiple pigmented 230 and/or optical modifying 240 layers, there may pigmented 230 and/or optical modifying 240 layers adjacent to both first outwardly facing major surface 222 or second outwardly facing major surface 224.

In use, flexible film 220 comprising patch 200 is arranged and configured to cover a skin blemish. Here, the pigmented layer 230 and at least one optical modifying layer 240 (region adapted to modify one or more optical properties) are arranged and configured to correspond to unblemished skin.

Figure 7:
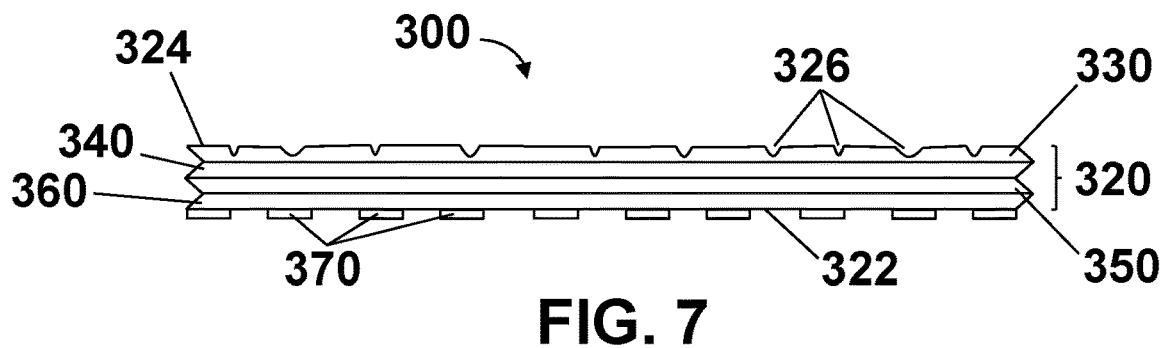
FIG. 7 is a cross-sectional view of a fourth embodiment of a camouflage make-up patch of the present invention in the x-z plane.

FIG. 7 is a cross-sectional view of a fourth embodiment of a camouflage make-up patch 300 of the present invention in the x-z plane. The figure shows patch 300 having a flexible film 320 having a first outwardly facing major surface 322, and a second outwardly facing major surface 324. First outwardly facing major surface 322 has a non-continuous adhesive layer 370 so as to be adhesive to the skin of the user. Though shown as non-continuous, adhesive layer 370 may be a continuous layer of adhesive, or may have discrete regions of adhesive. In some embodiments, adhesive layer 370 may be a pressure sensitive adhesive. Second outwardly facing major surface 324 has surface texture elements 326 to substantially correspond to the concealed skin. The figure also shows flexible film 320 having a pigmented layer 330, as well as layers which optically modifies light transmission, light reflection, or light absorption. The optically modifying layers are termed transmission modifying layer 340, reflection modifying layer 350, and absorption modifying layer 360.

The surface texture elements 326 on second outwardly facing major surface 324 are shown as continuous lines of indentation on surface 324, and pigmented layer 330 contains pigments for matching the color of the user's skin in the region of camouflage make-up patch 300.

FIG. 7 shows camouflage make-up patch 300 with a single pigmented layer 330 as well as single transmission modifying 340, reflection modifying 350, and absorption modifying 360 layers. In other embodiments, patch 300 may have multiple pigmented 330 and/or optical modifying (340, 350, 360) layers. Also, FIG. 7 shows the order of layers, from second outwardly facing major surface 324, to first outwardly facing major surface 322 as: pigmented layer 330, transmission modifying layer 340, reflection modifying layer 350, and absorption modifying layer 360. In other embodiments, the order of layers may be different, depending on the needs of the camouflage make-up patch 300 user.

Matrix Materials

There are numerous matrix materials which may be used in both pigmented region/layers (30, 130, 230, and 330), and modifying regions (40, 140, 240, 340, 350, and 350). The list of materials include, but are not limited to, gelatin, agar, silicone elastomers such as MDX4-4210 (Dow Corning Corp.), Silastic medical adhesive silicone type A (Dow Corning Corp.), methicone, dimethicone, silanes, polyesters (such as PET), polyacrylates (such as PMMA), polycarbonates, polypropylenes, high and low density polyethylenes, polyethylene napthalates, polysulfones, polyether sulfones, polyurethanes, polyamides, cellulose acetate butyrate, polyvinyl butyral, polyvinyl chloride, polyvinylidenedifluoride (PVDF), fluorinated ethylene propylene (PEF), polyethylene fluoride, polyetherimide, PETG, ABS, SIS, polyimides, epoxy, PBT, PVDF, polybute-1-ene, poly(4-methylpentene-1), maleimide isobutene copolymer, hydroxyl poly(ether sulfone), urethane acrylate, acrylo silicone, silicone urethane copolymers, EVA, caprolactone, PLA, PGLA, EM/AGM copolymer (ethylene-methyl acrylate-glycidyl methacrylate), cellulose derivatives, polyimides, polyimide benzoxazoles, poly-benzoxazoles, cyclic olefin polymers, metal soaps, lecithin, waxes, nylon, latex and silicone rubbers, and mixtures thereof.

In some embodiments silicone crosslinked polymers such as XPLs as described in *Nature Materials* (DOI:10.1038/NMAT 4635, 15, 911-918, 2016)

Pigment Materials

Pigmented region 30 and pigmented layers (130, 230, and 330) contain pigments for matching the color of the user's skin in the region of camouflage make-up patch application. Pigmented regions/layers are formed by mixing colorants into a matrix which is a relatively neutral or colorless material.

Most pigments used in manufacturing are dry colorants that are ground into a fine powder and added to the matrix material. A colorant can be both a pigment and a dye depending on the matrix material it is used in.

Certified colors may be organic compounds or inorganic metal salts. Examples of useful inorganic pigments include metal oxides, such as iron oxides (yellow, red, brown or black), titanium dioxide (white), zinc oxide, chrome oxide (green), as well as other materials including ferric ammonium ferrocyanide (blue), manganese violet, ultramarine (a zeolite-based mineral containing small amounts of polysulfides) blue, talc, lecithin modified talc, zeolite, kaolin, lecithin modified kaolin, zirconium, carmine (the aluminum salt of carminic acid), mica, magnesium carbonate cadmium-barium red deep, yellow ochre, burnt sienna, and mixtures thereof. Also useful are transparent metal oxide-coated silica beads.

Iron oxides, also known as cosmetic russets, have various colors which are classified into three major color groups: yellow iron oxide (ferric oxide-hydrate, or FeO(OH)), red colcothar (Ferric oxide, Fe2O3) and black iron oxide (Ferrous ferric oxide, or Fe3O4 (Fe2O3/FeO)). Various skin colors are produced by mixing these three groups of iron oxides in different ratios.

Examples of useful inorganic pigments include natural colorants and synthetic monomeric and polymeric colorants. Exemplary are phthalocyanine blue and green pigment, diarylide yellow and orange pigments, and azo-type red and yellow pigments such as toluidine red, litho red, naphthol red and brown pigments. Also useful are lakes, which are pigments formed by the precipitation and absorption of organic dyes on an insoluble base, such as alumina, barium, or calcium hydrates. Particularly preferred lakes are primary FD&C or D&C Lakes and blends thereof. Stains, such as bromo dyes and fluorescein dyes can also be employed.

Optical Modifiers

Optical modifying regions 40 and optical modifying layers (140, 240, 340, 350, and 360) modify one or more of the following properties: transmission, reflection, and absorption of light. Optical modifying regions/layers are formed by mixing optical modifiers into a matrix of a relatively neutral or colorless material.

Optical modifiers include materials that absorb light, reflect light, scatter light, opacifiers, and interference pigments.

Light absorbing materials include: para-aminobenzoic acid, para-aminobenzoic acid esters, cinoxate, anthralinate, cinnamate, homosalate, benzones, coffee powders and mixtures of these.

Light reflecting materials include: titanium dioxide, talc, zinc oxide, and mixtures of these.

Light scattering materials include powders such as: calcium aluminum boro silicate (Luxsil™), PMMA (Microsphere M-100), polyethylene (polyethylene Cl 2080), methyl methacrylate cross polymer (Covabeads LH85), nylon-12 (Orgasol 2002 O NatCos C), aluminum oxide (Al2O3), ethylene/acrylic acid copolymer (Flobeads EA209) and mixtures of two or more powders. These powders, when used, are present in an amount of from about 0.001% to about 20%, preferably about 1% to about 10%, by weight of the total composition.

Opacifiers include: Georgia kaolin powder neutral, kaolin powder calcined, Artskin white, dry pigment titanium (Ti) white, or Ti white artists' oil color, and mixtures of these.

Interference pigments include: micas layered with 50-300 nm films of TiO2, Fe2O3, or Cr2O3. Such pigments are often pearlescent, and may be uncoated or coated. Coatings include, but are not limited to, silica, nylon or polymethyl-methacrylate (PMMA). Useful interference pigments are available commercially from a wide variety of suppliers, for example, Rona (Timiron™ and Dichrona™), Presperse (Flonac™), Englehard (Duochrome™), and Kobo (SK-45-R and SK-45-G). Examples of particularly useful products are a mica coated with a thin layer of TiO2 and further coated with beads of PMMA (Kobo-LSBPA050/MicaR), which yields an attractive red color without the undesirable pearliness; and Flamenco Red (Engelhard), a TiO2 coated mica. A useful size range of the interference particles is from about 1 to about 200 p, and preferably is about 3 to about 100 g. The interference pigment is used in an amount of from about 0.05%-90% by weight, with the high end of the range being most appropriate for use in a pressed powder product. However, in most types of products, the amounts of interference pigment will range from about 0.5% to about 15%, the lower end of the range being used in un-pigmented (i.e., having no non-interference pigments) or lightly pigmented products, and the higher end of this range being used in more heavily pigmented products.

In some embodiments, the flexible films 20, 120, 220, and 320 comprising patches 10, 100, 200, and 300 of the present invention contain at least one active substance, active agent, or benefit agent. The benefit agents that may be used in film structures of the invention include cosmetic agents and therapeutic agents. Such substances may be any of a variety of compositions, including, without limitation, hyaluronic acid; hydroxyl acids (e.g., glycolic acid, lactic acid, malic acid, salicylic acid, citric acid, tartaric acid); anti-acne agents (e.g., salicylic acid, retinol, retinoids, or other keratolytics, and benzoyl peroxide, or other antimicrobial agents used to treat acne); shine control agents (e.g., rice protein, cotton powder, elubiol (dichlorophenyl-imidazoltioxolan); a retinoid or its derivative such as tretinoin, isotretinoin, motretinide, adapalene, tazarotene, azelaic acid, and retinol; a 5-alpha-reductase inhibitor of amino acids, e.g., glycine derivatives; hydrolyzed vegetable proteins, including soy protein and wheat protein, etc.; green tea (*Camellia sinesis*) extract, and cinnamon bark extract); moisturizers; antimicrobial agents (e.g., cationic antimicrobials such as benzylkonium chloride, benzethonium chloride, triclocarbon, polyhexamethylene biguanide, cetylpyridium chloride, methyl and benzothonium chloride; salts of chlorhexidine, such as Iodopropynyl butylcarbamate, diazolidinyl urea, chlorhexidene digluconate, chlorhexidene acetate, chlorhexidine isethionate, and chlorhexidene hydrochloride; halogenated phenolic compounds, such as 2,4,4'-trichloro-2-hydroxy diphenyl ether (Triclosan); parachlorometa xylenol (PCMX); short chain alcohols, such as ethanol, propanol, and the like); antibiotics or antiseptics (mupirocin, neomycin sulfate bacitracin, polymyxin B, 1-ofloxacin, tetracyclines (chlortetracycline hydrochloride, oxytetracycline-10hydrochloride and tetracycline hydrochloride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs), anti-inflammatory agents (e.g., suitable steroidal anti-inflammatory agents such as corticosteroids such as hydrocortisone, hydroxyl triamcinolone alpha methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butyl ester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluorometholone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts, nonsteroidal anti-inflammatory agents, feverfew (*Tanacetum parthenium*), goji berry (*Lycium barbarum*), milk thistle extract (*Silybum marianum*), amaranth oil (*Amaranthus cruentus*), pomegranate (*Punica granatum*), yerbe mate (Ilex paraguariensis leaf extract), white lily flower extract (*Lilium Candidum*), olive leaf extract (*Olea europaea*) and phloretin (apple extract)); antimycotic/antifungal agents (e.g., miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs; an azole, an allylamine, or a mixture thereof); external analgesics (e.g., ibuprofen- or diclofenac; capsaicin, fentanyl, and salts thereof such fentanyl citrate; paracetamol (as acetaminophen); non-steroidal anti-inflammatory drugs (NSAIDs) such as salicylates; opioid drugs such as morphine and oxycodone; ibuprofen- or diclofenac-containing gel); antioxidants (e.g., sulfhydryl compounds and their derivatives (e.g., sodium metabisulfite and N-acetyl cysteine), lipoic acid and dihydrolipoic acid, resveratrol, lactoferrin; ascorbic acid, ascorbic acid esters, and ascorbic acid derivatives (e.g., ascorbyl palmitate and ascorbyl polypeptide); butylhydroxy anisole, butylated hydroxytoluene (butylhydroxy toluene), retinoids (e.g., retinol and retinyl palmitate), tocopherols (e.g., tocopherol acetate), tocotrienols, and ubiquinone; cysteine, N-acetylcysteine, sodium bisulfite, sodium metabisulfite, sodium formaldehydesulfoxylate, acetone sodium bisulfite, tocopherols, and nordihydroguaiaretic acid; extracts containing flavonoids and isoflavonoids and their derivatives (e.g., genistein and diadzein); extracts containing resveratrol and the like; grape seed, green tea, pine bark, and propolis; plant-derived polyphenol antioxidants such as clove, cinnamon, oregano, turmeric, cumin, parsley, basil, curry powder, mustard seed, ginger, pepper, chili powder, paprika, garlic, coriander, onion and cardamom; typical herbs such as sage, thyme, marjoram, tarragon, peppermint, oregano, savory, basil and dill weed)); depilatory agents (e.g., calcium thioglycolate or potassium thioglycolate); vitamins (e.g., Vitamin A, Vitamin B, Vitamins C, Vitamin E; either alpha, beta, gamma or delta tocopherols, niacin or niacinamide) and vitamin salts or derivatives such as ascorbic acid diglucoside and vitamin E acetate or palmitate; sunblock (e.g., titanium dioxide) and/or sunscreen (e.g., inorganic sunscreens such as titanium dioxide and zinc oxide; organic sunscreens such as octyl-methoxy cinnamates, octyl salicylate, homosalate, avobenzone); vasodilators (e.g., niacin); humectants (e.g., glycerin); anti-aging agents (e.g., retinoids; dimethylaminoathanol (DMAE), copper containing peptides); alpha hydroxy acids or fruit acids and their precursors such as glycolic acid, citric acid, lactic acid, malic acid, mandelic acid, ascorbic acid, alpha-hydroxybutyric acid, alpha-hydroxyisobutyric acid, alphahydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, rice, oat (in colloidal and/or oil forms), shitake, seaweed, blackberry, southern wood, lotus, wheat, and safflower, and salts and prodrugs thereof); carotenoids, ceramides, fatty acids, enzymes, enzyme inhibitors, minerals, steroids, peptides, amino acids, botanical extracts, colorants, etc. The substances may affect the skin in any of a variety of manners, such as by moisturizing; enhancing skin tone or color (such as with pigments); treating or at least mitigating various skin conditions (such as dry or severe dry skin, eczema, psoriasis, atopic dermatitis, allergic rashes, acne, blackheads, pustules, comedones, rosacea, shingles, wrinkles, cold sores, herpes, corns, warts, sunburn, insect bites, poison ivy, etc.); applying a mechanical force (such as shrinkage) to smooth wrinkles; or, more generally, treating or mitigating the symptoms and appearance of undesired skin imperfections (such as under eye dark circle, redness of acne, fine lines and wrinkles, post inflammatory hyperpigmentation (PIH), redness, inflammation, cellulite, wrinkles, age spots, mottled pigmentation, dark spots, liver spots, under eye puffiness); removing unwanted facial or body hair; aiding in wound healing; etc. For instance, lotions, creams, oils, and even masks may be applied to skin to treat or otherwise to affect the skin. Such personal or consumer healthcare substances are absorbed into the skin generally following the principles of diffusion, under which the rate of diffusion or transport across the skin is correlated with the difference in active concentration on both sides of the skin.

In some embodiments, the camouflage make-up patch of the present invention is a personalized consumer color-matching patch that disguises unwanted blemishes and skin conditions while delivering formulations and active agents. The patch provides superior camouflage of unwanted skin conditions and blemishes by utilizing diagnostic and imaging technology to analyze the consumer's skin area to treat and camouflage resulting in a fully personalized skin solution. Advantages include: superior blemish concealment and camouflage, a fast and non-skin irritating method of blemish concealment compared to standard make-up, and longer lasting performance and durability compared to make-up.

In some embodiments, a smart-phone, or equivalent image-capturing device, is used in combination with computer vision and machine learning to collect personalized skin information (shape/geometry, micro-geometry and gloss, color, translucency). Utilizing a computer simulation program, such as CONTONING, a high level of accuracy and natural patient skin properties, such as shape, micro-geometry, texture, gloss, color, translucency, are simulated via MULTI-MATERIALS and the CONTONING technology. The result is an "inpainting" (changing appearance of problematic skin to a desired state) recommendation to the patient to address the unwanted skin condition.

In some embodiments, using Artificial Intelligence and Diagnostics, a treatment recommendation is made via supervised machine learning w/expert annotated skin images and incorporating user preferences feedback. The computer model then uses CNN's (Convolutional Neural Networks) to recommend accurate treatment predictions.

The camouflage make-up patch of the present invention can be produced using Additive Manufacturing technology. Additive Manufacturing is a group of techniques used to quickly fabricate a physical part or assembly using three-dimensional computer aided design (CAD) data. Construction of the part or assembly is usually done using "additive layer manufacturing" technologies such as 3D printing. Additive manufacturing is a simple, effective, and economically method of making camouflage make-up patches with multiple layers and surface features.

In general, the computer-aided-design-computer-aided manufacturing CAD-CAM workflow is the traditional additive manufacturing process. The process starts with the creation of geometric data, either as a 3D solid using a CAD workstation, or 2D slices using a scanning device. For Additive Manufacturing, this data must represent a valid geometric model; namely, one whose boundary surfaces enclose a finite volume, contains no holes exposing the interior unless they are designed into the structure, and do not fold back on themselves. In other words, the object must have an "inside." The model is valid if for each point in 3D space the algorithm can determine uniquely whether that point lies inside, on, or outside the boundary surface of the model. CAD post-processors will approximate the internal CAD geometric forms with a simplified mathematical form, which in turn is expressed in a specified data format which is a common feature in Additive Manufacturing. To obtain the necessary motion control trajectories to drive the Additive Manufacturing mechanism, the prepared geometric model is typically sliced into layers, and the slices are scanned into lines (producing a "2D drawing" used to generate trajectory as in computer numerical control toolpath), resulting in a layer-to-layer physical building process.

The 3D printing process enables the creation of different sizes and shapes camouflage make-up patch, as well as the ability to produce multi-layer patches arrays with more than one material. Soft materials, hard materials, and even liquids can be incorporated into individual layers or regions. Incompatible compounds may also be built into different sections of the camouflage make-up patch without cross contamination fears.

Patches 10, 100, 200, and 300 of the present invention may be used as methods of camouflaging blemishes in a desired region of human skin. The method includes the steps of: (a) providing image data relating to the desired region of human skin to a computer, wherein the computer converts the image data to geometric data representing a geometric model of the desired region of human skin; (b) using the geometric data to control a 3D printer to print the patch for application to the desired region, and applying the patch to the desired region of skin.

In some embodiments, the geometric data may be used to determine a subregion of the human skin in need of a benefit agent. In these embodiments, the 3D printer prints a benefit agent in a subregion of the patch corresponding to the subregion of the human skin in needing the benefit agent.

EXAMPLES

Example 1: Single-Layer Camouflage Make-Up Patch

A single layer camouflage patch, with reference to FIGS. 1 to 3, comprising of a thin acrylic adhesive deposition, such as BASF acrylic adhesive, on one outer surface of the patch where the adhesive deposition can cover the entire surface or be strategically placed on first outwardly facing major surface 22, and a translucent natural skin matching color and texture finish on the second outwardly facing major surface 24. The entire single layer camouflage make-up patch 10 is 3D printed on a Stratasys OBJ260 Connex3 printer (Stratasys Ltd., Eden Prairie, Minn.), or equivalent, using a medical grade silicone elastomer, such as Silastic MDX4-4210 from Dow Corning Corporation (Midland, Mich.), that has pre-mixed colorants, such as red colcothar (Ferric oxide $Fe_2O_3$ from Clarke Colors LLC, Marietta, Ga.), and opacifiers, such as $TiO_2$ (Titanium dioxide (Sigma-Aldrich, #224227, mean size 1 μm and maximum size 5 μm)), to mimic the natural skin for color, transparency, reflectance, texture and opacity. One method of matching the human skin can be achieved by mixing suitable concentrations of $TiO_2$ particles and cosmetic powder/pigments, such as red colcothar (Ferric oxide $Fe_2O_3$), with the silicone rubber; this produces optical properties of human skin over a range of wavelengths from 400 to 1,000 nm. The durometer/hardness and elasticity of the medical grade silicone used to 3D print the patch also needs to match the human skin, typical values for human skin are 50-55 Shore A durometer for hardness having a flex modulus of approximately 7,000-12,000 psi depending on user skin characteristics and properties. The pigments and opacifiers are pre-mixed in the Additive Manufacturing (AM) jetting materials or mixed at the point of deposition during the 3D printing process. Additives can be added during the 3D printing process at strategic locations to mitigate desired skin conditions to be targeted, reference optical modifying regions 40a to 40f in FIG. 3. The actives, such as salicylic acid and retinol to treat acne, are deposited between the adhesive depositions to ensure direct skin contact for each additive. The carrier of the actives has the physical characteristics that allow it mimic the natural skin color, transparency, reflectance, texture and opacity thereby providing camouflage for the skin condition being treated.

Example 2: Multi-Layer Camouflage Make-Up Patch

A three-layer embodiment example for a multi-layer camouflage make-up patch 200, with reference to FIG. 6, comprising of a first thin acrylic (such as BASF acrylic adhesive) adhesive layer 250, where the adhesive deposition can create the entire layer or be strategically placed to allow deposition of actives in the open areas thus allowing the actives the ability to contact the skin and treat specific skin conditions. In this three-layer camouflage make-up patch 200 construction, optical modifying layer 240 is constructed using a medical grade silicone elastomer, such as SILASTIC® MDX4-4210 from Dow Corning Corporation (Midland, Mich.), that has pre-mixed opacifiers, such as $TiO_2$ (Titanium dioxide (Sigma-Aldrich, #224227, mean size 1 µm and maximum size 5 µm)), to mimic the natural skin for transparency, reflectance, and opacity. Optical modifying layer 240 can also be constructed to include actives to mitigate certain skin conditions by selectively 3D printing the desired actives over the initial adhesive/actives of adhesive layer 250. Once actives of adhesive layer 250 dissolve into the skin, the 3D printed actives behind the dissolved actives of the adhesive layer 250 are exposed to the skin surface and can act upon the skin condition to be treated. Pigmented layer 230, is also constructed of medical grade silicone elastomer, such as Silastic MDX4-4210 from Dow Corning Corporation (Midland, Mich.), that has pre-mixed colorants, such as red colcothar (Ferric oxide $Fe_2O_3$ from Clarke Colors LLC, Marietta, Ga., mean size 1 µm and maximum size 5 µm), to mimic the natural skin for color, transparency, reflectance, texture and opacity of the skin. The entire multi-layer camouflage make-up patch 200, is 3D printed on a Stratasys OBJ260 Connex3 printer (Stratasys Ltd., Eden Prairie, Minn.), or equivalent. The durometer/hardness and elasticity of the medical grade silicone used to 3D print the patch also needs to match the human skin, typical values for human skin are 50-55 Shore A durometer for hardness having a flex modulus of approximately 7,000-12,000 psi depending on user skin characteristics and properties. The pigments and opacifiers are pre-mixed in the Additive Manufacturing (AM) jetting materials or mixed at the point of deposition during the 3D printing process. Additives can be added during the 3D printing process at strategic locations in to mitigate desired skin conditions to be targeted, in pigmented layer 230 or optical modifying layer 240. The actives, such as salicylic acid and retinol to treat acne, are deposited between the adhesive depositions to ensure direct skin contact for each additive. The carrier of the actives has the physical characteristics that allow it mimic the natural skin color, transparency, reflectance, texture and opacity thereby providing camouflage for the skin condition being treated.

The specification, embodiments, and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. A method of camouflaging a blemish in a desired region of human skin comprising the steps of:
   (a) providing image data relating to the desired region of human skin to a computer, wherein the computer converts the image data to geometric data representing a geometric model of the desired region of human skin;
   (b) using the geometric data to control a 3D printer to print successive layers of flexible materials to form a patch for application to the desired region of human skin comprising a flexible film having a first, adhesive, outwardly facing major surface and a second outwardly facing surface which is textured to correspond to skin covered by the patch during use; wherein the flexible film further comprises at least one pigmented region and at least one region adapted to modify one or more optical properties selected from the group consisting of light transmission, light reflection, and light absorption; and
   (c) applying the patch to the desired region of human skin.

2. The method of claim 1 further comprising using the geometric data to determine a subregion of the human skin in need of a benefit agent.

3. The method of claim 2 wherein the 3D printer prints a benefit agent in a subregion of the patch corresponding to the subregion of the human skin in need thereof.

4. The method of claim 3 wherein the benefit agent comprises an antibiotic.

\* \* \* \* \*